United States Patent [19]

Oberhausen et al.

[11] Patent Number: 4,885,151
[45] Date of Patent: Dec. 5, 1989

[54] DIAGNOSTIC AID FOR THE SCINTIGRAPHIC VISUALIZATION OF MALIGNANT TUMORS COMPRISING THE SUBSTANCE OBTAINED FROM ENZYMATIC PROCESSING OF MUREIN USING HEN'S EGGWHITE LYSOZYME

[75] Inventors: Erich Oberhausen, Homburg/Saar; Ludwig Kuhlmann, Hofheim am Taunus; Gerhard Seibert, Darmstadt; Axel Steinstrasser, Liederbach; Hans-Joachim Schroth, Hanau; Karl-Heinz Bremer, Bad Soden am Taunus, all of Fed. Rep. of Germany

[73] Assignee: Hoechst Aktiengesellschaft, Frankfurt am Main, Fed. Rep. of Germany

[21] Appl. No.: 66,185

[22] Filed: Jun. 25, 1987

[30] Foreign Application Priority Data

Jun. 27, 1986 [DE] Fed. Rep. of Germany ....... 3621570

[51] Int. Cl.$^4$ ....................... A61K 49/02; C09K 11/04
[52] U.S. Cl. .......................................... 424/1.1; 424/9; 252/625; 252/645
[58] Field of Search ..................... 424/1.1, 9; 252/625, 252/645

[56] References Cited

U.S. PATENT DOCUMENTS 4,364,920 12/1982 Winchell .
4,590,060 5/1986 Ehrenfeld ............................ 424/1.1
4,596,769 6/1986 Shockman et al. .............. 424/1.1 X

FOREIGN PATENT DOCUMENTS 0133553 2/1985 European Pat. Off. ............ 436/547

OTHER PUBLICATIONS

Weidel et al., Avd. & Enzymol., 26, 193–232 (1964).
Schumichen et al., Nucl. Med., 25, pp. 28–30, (1986).
Primosigh et al., Chem. Abst., Aug. 1961, No. 16674f–16674g.
Keenan, A. et al., "Monoclonal Antibodies in Nuclear Medicine", J. Nucl. Med., vol. 26, No. 5, pp. 531–537, 1985.
Glauner, B. et al., "The Analysis of Murein Composition With High–Pressure–Liquid Chromatography", The Target of Penicillin, Berlin, pp. 30–34, 1983.

*Primary Examiner*—John S. Maples
*Attorney, Agent, or Firm*—Finnegan, Henderson, Farabow, Garrett and Dunner

[57] ABSTRACT

A diagnostic aid for the scintigraphic visualization of malignant tumors which contains a radionuclide which is bonded by means of a complex-forming agent to the substance obtained by the enzymatic processing of murein with enzyme consisting essentially of hen's eggwhite lysozyme.

5 Claims, 1 Drawing Sheet

DIAGNOSTIC AID FOR THE SCINTIGRAPHIC VISUALIZATION OF MALIGNANT TUMORS COMPRISING THE SUBSTANCE OBTAINED FROM ENZYMATIC PROCESSING OF MUREIN USING HEN'S EGGWHITE LYSOZYME

BACKGROUND OF THE INVENTION

The invention relates to a diagnostic aid for the scintigraphic visualization of malignant tumors, to a method for the scintigraphic visualization of malignant tumors using this diagnostic aid, and to a process for the preparation of the diagnostic aid.

There has long been a desire to have available a diagnostic aid which allows the size and position of malignant tumors to be established at an early stage. There has been no lack of attempts to attain this object by means of nuclear medical methods which may sensitively detect and provide images of the distribution pattern in the human body of substances coupled to γ-emitting nuclides. The success of these methods depends on whether it is possible to find substances which accumulate specifically or non-specifically in malignant tumors.

It is now hardly possible to keep track of the number of tumor-associated substances which have already been used for tumor scintigraphy, but these substances are not tumor-specific, and their affinity for tumors is often unknown. These include inorganic substrates such as gallium-67 citrate, indium-111 chloride and bismuth-206 chloride. However, products of tumor metabolism, such as nitrogen-13-glutamate and selenium-75-methionine, have also already been used for the detection of tumors by scintigraphy (cf. E. Henze, "Szintigraphische Lokalisationsdiagnostik von Tumoren" (Diagnostic Localization of Tumors by Scintigraphy), Munch. med. Wschr. 127, 182–184 (1985)). Finally, radiolabeled cytostatics such as cobalt-57-bleomycin, or tumor-associated proteins such as iodine-131-antifibrin, have also been used already. It is common to all these substances that they often accumulate in the tumor only in low concentrations, so that unambiguous determination of the position of the tumor is impossible, especially in cases where the tumor foci are small.

However, in recent years tumor scintigraphy has also made considerable advances owing to the availability of radiolabeled, tumor-specific monoclonal antibodies or their immunologically active fragments (cf. A. M. Keenan, J. C. Harbert and S. M. Larson, "Monoclonal Antibodies in Nuclear Medicine", The Journal of Nuclear Medicine, Volume 26, 531–537 (1985)). An improvement in the in vivo kinetics of these antibodies has already produced very encouraging results. The techniques of nuclear medicine which are available permit quantitative and tomographic visualization. However, there has as yet been no extensive clinical experience of the sensitivity, specificity or side effects, because of the heterogeneity of the antibodies which have been used to date. An additional factor is that monoclonal antibodies are able to attach themselves only to the tumors which have the exactly corresponding antigen on the cell surface. Thus, the high specificity of the monoclonal antibodies does not allow general detection of tumors of interest.

Moreover, European Patent Application 142,641 has disclosed an agent for the diagnosis and therapy of tumors which contains an immunomodulator labeled with a radioactive emitter, a dyestuff or a cytostatic. This agent is preferably administered together with a cocktail composed of an aldehyde and an alcohol. The preferred immunomodulators are understood to include muramyldipeptide derivatives, peptidoglycans or peptidoglycan-free extracts from certain bacterial species. Tumor detection was possible in patients who had drunk the said cocktail 30 minutes before administration of the diagnostic aid.

SUMMARY OF THE INVENTION

A diagnostic aid for the scintigraphic visualization of malignant tumors has been discovered, which contains a radionuclide which has been bonded by means of a complex-forming agent to the substance obtained by the enzymatic processing of murein with enzyme consisting essentially of hen's eggwhite lysozyme.

DESCRIPTION OF THE PREFERRED EMBODIMENTS

Figure 1:
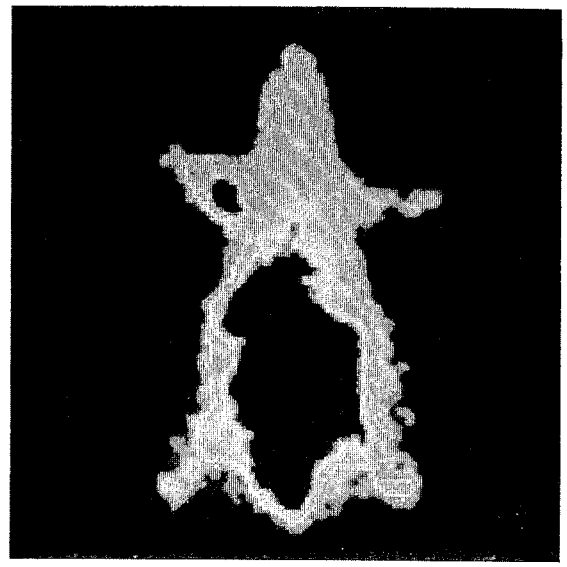
FIG. 1 is a scintigram of a Walker 256 carcinoma that was detected using a diagnostic aid in accordance with this invention.

It has now been found that it is possible to dispense with administration of a cocktail composed of an aldehyde and an alcohol when a diagnostic aid which contains a substance which is obtained in the enzymatic processing of murein, and to which a radionuclide is bonded by means of a complex-forming agent, is used for the scintigraphic visualization of malignant tumors.

The substance obtained by the enzymatic processing of murein comprises a mixture of components such as are described by, for example, B. Glauner and U. Schwarz in "The Analysis of Murein with HPLC" in The Target of Penicillin, pages 29–34, Berlin 1983. In addition there is a contribution from cyclic muropeptides, for example muropeptide $C_4$, as described in W. Weidel and H. Pelzer, Adv. in Enzymol. 26, 193–232 (1964) and a contribution from higher molecular weight murein fragments, of molecular weight up to about 10,000.

This substance is obtained by suspending the murein from *E. coli* cells, which has been prepared by the processes known from the literature, (10 mg/ml) in 0.05M ammonium acetate, and incubation with 10 μg/ml hen's eggwhite lysozyme at 37° C. for 18 hours. Sedimentation of insoluble constituents at 50,000×g is followed by extraction with chloroform and drying of the aqueous phase. Ammonium acetate is removed at 50° C. in vacuo over the course of 65 hours.

A complex-forming agent, such as ethylenediaminetetraacetic acid, diethylenetriaminepentaacetic acid or nitrilotriacetic acid, which carries a radionuclide is bonded to the free amino groups of this substance. Technetium-99m or indium-111 are preferably used for this purpose.

It is a particular advantage that the diagnostic aid according to the invention can be prepared by processing the cell walls of any desired bacteria. Hence, it is preferably obtained from *Escherichia coli* because this microorganism can be obtained commercially as frozen cell mass. The substance obtained by the enzymatic processing of murein is expediently allowed to react with the complex-forming agent at room temperature. After the excess complex-forming agent has been removed, the solution is freeze-dried and mixed with the desired activity of radionuclide. This is followed by sterilization by filtration and adjustment to the desired activity concentration using isotonic sodium chloride solution.

Surprisingly, the diagnostic aid obtained in this way is suitable for the visualization of a wide variety of malignant tumors. Both soft-tissue tumors and bone tumors can be readily detected.

The preparation and the use of the diagnostic aid are illustrated by the examples which follow:

EXAMPLE 1

Attachment of diethylenetriaminepentaacetic acid (DTPA)

10 mg of murein from *E. coli* which has been enzymatically processed by generally known processes is dissolved in 0.5 ml of 0.05M bicarbonate buffer, pH 8.2, and, at room temperature, 10 mg of bicyclic DTPA anhydride are added, and the mixture is left to stand at room temperature for 10 min. The excess DTPA is removed by chromatography (support material: silica gel RP-18; mobile phase: 0.1M phosphate solution, pH 4.69, and methanol:water, 70:30). The resulting solution of the product is divided into portions and freeze-dried.

EXAMPLE 2

Reaction with indium-111

The lyophilizate is dissolved in 0.1M ammonium citrate buffer, pH 6.5, and mixed with the desired activity, for example 100 MBq, of indium-111 citrate at room temperature. The indium-111 citrate is prepared from the commercially available indium-111 chloride by 1:1 dilution with 0.1M ammonium citrate, pH 6.5. After the solution has stood at room temperature for 10 min it is sterilized by filtration through a filter and adjusted to the desired activity concentration with isotonic sodium chloride solution. The radiochemical purity can be checked by high-performance liquid chromatography.

Support material: Silica gel RP-18
Mobile phase:
20 min; 0.1M $H_3PO_4$, pH 4.69
120 min 0–100%; 0.1M $H_3PO_4$, pH 4.69, +15% $CH_3OH$ After filtration through the sterilizing filter, the product is ready for injection. The labeling procedure can be carried out both by the manufacturer and by the user.

EXAMPLE 3

Animal experiment

A Walker 256 carcinoma (soft-tissue tumor) was implanted in the muscle of the right foreleg of a rat (Sprague-Dawley). After it had been established that the tumor had developed normally, the animal was given an intravenous injection of 0.5 ml (0.3 MBq of indium-111) of the product. The scintigram obtained after 2 h is depicted in FIG. 1. The margins of the tumor can be clearly seen in the right foreleg. The tumor/muscle ratio was 4.

EXAMPLE 4

Animal experiment

Figure 2:
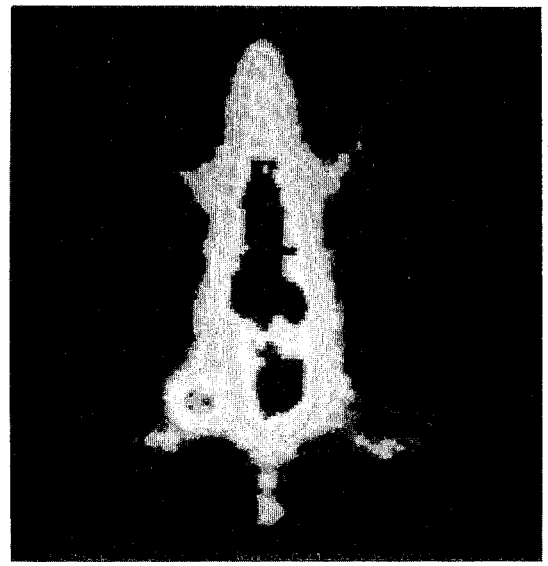
FIG. 2 is a scintigram of an osteosarcoma that was detected using a diagnostic aid in accordance with this invention.

A rat (Sprague-Dawley) which had had an osteosarcoma (bone tumor) implanted in the right hindleg received i.v. administration of 0.5 ml (0.3 MBq of indium-111) of the product. The tumor can be located unambiguously in the scintigram after 2 h (FIG. 2). The measured tumor/muscle ratio was likewise 4.

We claim:

1. A diagnostic aid for the scintigraphic visualization of malignant tumors, which contains a radionuclide which has been bonded by means of a complex-forming agent to the substance obtained by the enzymatic processing of murein with enzyme consisting essentially of hen's eggwhite lysozyme.

2. A method for the scintigraphic visualization of malignant tumors in a patient, which comprises injection of an effective amount of the diagnostic aid as claimed in claim 1 into the patient, and determination of the diagnostic aid in the body.

3. A diagnostic aid as claimed in claim 1, wherein technetium-99m or indium-111 are used as the radionuclide.

4. A diagnostic aid as claimed in claim 1, wherein the murein is obtained from *Escherichia coli*.

5. A diagnostic aid as claimed in claim 1, wherein diethylenetriaminepentaacetic acid is used as the complex-forming agent.

* * * * *